United States Patent [19]

Safavy et al.

[11] Patent Number: 5,756,825
[45] Date of Patent: May 26, 1998

[54] HYDROXAMIC ACID-BASED BIFUNCTIONAL CHELATING COMPOUNDS

[76] Inventors: Ahmad Safavy, 2612 Rime Village, Birmingham, Ala. 35216; Donald J. Buchsbaum, 1013 32nd St. South, Birmingham, Ala. 35205; Mohammad Bagher Kazaeli, 11 Glen Iris Park, Birmingham, Ala. 35205

[21] Appl. No.: 48,869

[22] Filed: Apr. 16, 1993

Related U.S. Application Data

[63] Continuation of Ser. No. 941,986, Sep. 8, 1992, abandoned.

[51] Int. Cl.$^6$ .................... C07C 229/00; C07C 239/00
[52] U.S. Cl. .................... 560/169; 560/312; 562/448; 562/561; 562/621; 562/623; 534/10; 534/14; 534/15; 534/16; 424/1.53; 424/1.65; 424/1.69; 424/9.34
[58] Field of Search .................... 534/10, 14, 15, 534/16; 564/152, 153, 123; 558/250; 560/1, 147, 155, 157, 169, 312; 424/1.1, 9, 85.8; 530/391.3, 391.5; 562/448, 561, 621, 623

[56] References Cited

U.S. PATENT DOCUMENTS

| | | | |
|---|---|---|---|
| 3,471,476 | 10/1969 | Gaeumann et al. | 260/239.3 |
| 4,311,688 | 1/1982 | Burchiel et al. | 424/1 |
| 4,331,647 | 5/1982 | Goldenberg | 424/1 |
| 4,348,376 | 9/1982 | Goldenberg | 424/1 |
| 4,361,544 | 11/1982 | Goldenberg | 424/1 |
| 4,444,744 | 4/1984 | Goldenberg | 424/1.1 |
| 4,460,561 | 7/1984 | Goldenberg | 424/1.1 |
| 4,472,509 | 9/1984 | Gansow et al. | 436/548 |
| 4,485,086 | 11/1984 | Wong | 424/1.1 |
| 4,504,492 | 3/1985 | Wilkinson et al. | 514/522 |
| 4,618,708 | 10/1986 | Roques et al. | 562/448 |
| 4,624,846 | 11/1986 | Goldenberg | 424/1.1 |
| 4,652,440 | 3/1987 | Paik et al. | 424/1.1 |
| 4,671,958 | 6/1987 | Rodwell et al. | 424/85 |
| 4,687,841 | 8/1987 | Spilburg et al. | 530/331 |
| 4,741,900 | 5/1988 | Alvarez et al. | 424/85 |
| 4,771,038 | 9/1988 | Wolanin et al. | 514/18 |
| 4,778,672 | 10/1988 | Deutsch et al. | 424/1.1 |
| 4,824,659 | 4/1989 | Hawthorne | 424/1.1 |
| 4,831,122 | 5/1989 | Buchsbaum et al. | 530/389 |
| 4,839,467 | 6/1989 | Deutsch | 534/10 |
| 4,867,962 | 9/1989 | Abrams | 424/1.1 |
| 4,915,733 | 4/1990 | Matwiyoff | 424/9 |
| 4,918,105 | 4/1990 | Cartwright et al. | 514/575 |
| 4,925,925 | 5/1990 | Deutsch | 534/18 |
| 4,939,299 | 7/1990 | Coleman et al. | 562/623 |
| 4,966,997 | 10/1990 | Shanzer et al. | 562/623 |
| 5,021,236 | 6/1991 | Gries et al. | 424/9 |
| 5,059,541 | 10/1991 | Fritzberg et al. | 436/501 |
| 5,101,041 | 3/1992 | Troutner et al. | 548/518 |
| 5,175,191 | 12/1992 | Marks et al. | 514/575 |
| 5,202,451 | 4/1993 | Fritzberg et al. | 556/419 |
| 5,225,173 | 7/1993 | Wai | 423/2 |
| 5,268,384 | 12/1993 | Galardy | 514/419 |
| 5,326,778 | 7/1994 | Rosebrough | 514/387 |
| 5,387,610 | 2/1995 | Gray et al. | 514/575 |

OTHER PUBLICATIONS

Bhargara et al., "Hydroxamic Acid Derivatives . . . ", Abstract, *194th National Meeting of the American Chemical Society*, 1987.

Nakayama et al., "Hydroxamide as a chelating Moiety for Preparation of Tc–99m Radiopharmaceuticals", *Journal of Nuclear Medicine*, May 1992, p. 1102, abstract No. 819.

(List continued on next page.)

*Primary Examiner*—John Kight
*Assistant Examiner*—Lara C. Kelley

[57] ABSTRACT

The present disclosure details the preparation of hydroxamic-acid based bifunctional chelators and their use in conjugating metal ions to proteins and nucleic acids for tumor or tissue imaging or therapy purposes. Some preferred aspects of the disclosure involve the preparation of trisuccin, chemical name N-[tris(2-N-benzyloxyaminocarbonylethyl)] methylsuccinamic acid, which is a hydroxamic acid/succinate based structure that is particularly useful for binding radionuclides such as $^{99m}$Tc, $^{186}$Re and $^{67}$Cu.

4 Claims, 6 Drawing Sheets

(i) DCC, HOBT, THF, CHCl$_3$; (ii) TFA; (iii) BnO–NH$_2$·HCl, DIISOPROPYLETHYLAMINE, DCC, HOBT, THF, CHCl$_3$; (iv) LiOH·H$_2$O, THF/H$_2$O+ –WORK–UP; (v) H$_2$·Pd/C (10%).

OTHER PUBLICATIONS

Nakayama et al., "Evaluation of Tc–99m Hydroxamic Acids as Tumor Imaging Agents", *Journal of Nuclear Medicine*, May 1992, pp. 988–989, abstract No. 693.

International Search Report, mailed Dec. 16, 1993.

Abrams, Michael J. "Small Coordination Complexes in Tumor Imaging." *J. Nucl. Med.*, 32(5):849–850, 1991.

Abrams et al., "Technetium–99m–Human Polyclonal IgG Radiolabeled via the Hydrazino Nicotinamide Derivative for Imaging Focal Sites of Infection in Rats," *J. Nucl. Med.*, 31(12):2022–2028, 1990.

Alauddin et al., "An Improved Method of Direct Labeling Monoclonal Antibodies with $^{99m}$Tc," *Nucl. Med. Biol.*, 19(4):445–454, 1992.

Alauddin et al., "Evaluation of $^{99m}$Tc–Labeled $N_2S_4$ Coupled B72.3 and Lym–1 Antibodies as Tumor–Imaging Agents in Tumor–Bearing Nude Mice," *Antibody Immunoconjugates, Radiopharm.*, 4(3):331–337, 1991.

Arano et al., "In the Procurement of Stable $^{99m}$Tc Labeled Protein Using Bifunctional Chelating Agent," *Appl. Radiat. Isot.*, 37(7):587–592, 1986.

Arano et al., "Synthesis and Evaluation of a New Bifunctional Chelating Agent for $^{99m}$Tc labeling Proteins: p–Carboxyethylphenylglyoxal–di (N–methylthiosemicarbazone)." *J. Nucl. Med. Biol.*, 12(6):425–430, 1986.

Arano et al., "Technetium–99m–Labeled Monoclonal Antibody with Preserved Immunoreactivity and High In Vivo Stability," *J. Nucl. Med.*, 28(6:1027–1033, 1987.

Baidoo et al., "$^{99m}$Tc Labeling of Proteins: Initial Evaluation of a Novel Diaminedithiol Bifunctional Chelating Agent," *Canc. Res. (Suppl.)*, 50:799s–803s, 1990.

Balaban et al., "Radionuclide Imaging of Bone Marrow Metastases with a Tc–99m Labeled Monoclonal Antibody to Small Cell Lung Carcinoma," *Clin. Nucl. Med.*, 16:732–736, 1991.

Beaumier et al., "$^{186}$Re Radioimmunotherapy of Smal Cell Lung Carcinoma Xenografts in Nude Mice," *Canc. Res.*, 51:676–681, 1991.

Blend et al., "Role of Technetium 99m–Labeled Monoclonal Antibody in the management of Melanoma Patients," *J. Clin. Oncol.*, 10(8):1330–1337, 1992.

Breitz et al., "Clinical Experience with Rhenium–186–Labeled Monoclonal Antibodies for Radioimmunotherapy: Results of Phase I Trials," *J. Nucl. Med.* 33(6):1099–1109, 1992.

Britton et al., "Radiolabelled Monoclonal Antibodies in Oncology I. Technical Aspects," *Nucl. Med. Commun.*, 12:65–76, 1991.

Brown et al., "Pharmacokinetics of $^{99m}$Tc–Metallothionein–B72.3 and Its F(ab')$_2$ Fragment," *Canc. Res. (Suppl.)* 50:835s–839s, 1990.

Buchsbaum and Lawrence, "Tumor Therapy with Radiolabeled Monoclonal Antibodies," *Antibody, Immunoconjugates, Radiopharm.*, 4(3):245–272, 1991.

Burchiel et al., "Pharmacokinetic Evaluation of Technetium–99–Metallothionein–Conjugated Mouse Monoclonal Antibody B72.3 in Rhesus Monkeys," *J. Nucl. Med.*, 30(8):1351–1357, 1989.

Chatterjee and Banerjee, "Functionalization of Hydroxy Compounds with Nitrilotriacetic Acid for Technetium–99m Chelation: Excretory Properties of the Radiolabelled Chelates," *Nucl. Med. Biol.*, vol. 18(3):263–274, 1991.

Childs and Hnatowich, "Optimum Conditions for Labeling of DTPA–Coupled Antibodies with Technetium–99m." *J. Nucl. Med.*, 26(3):293–299, 1985.

Eckelman and Volkert, "In Vivo Chemistry of $^{99m}$Tc–Chelates," *J. Appl. Radiat. Isot.*, 33:945–951, 1982.

Franz et al., "The Production of $^{99m}$Tc–Labeled Conjugated Antibodies Using a Cyclam–Based Bifunctional Chelating Agent," Nucl. Med. Biol., 14(6):569–572, 1987.

Fritzberg and Beaumier, "Targeted Proteins for Diagnostic Imaging: Does Chemistry make a Difference?," *J. Nucl. Med.*, 33(3):394–397, 1992.

Fritzberg et al., "Specific and Stable Labeling of Antibodies with Technetium–99m with a Diamide Dithiolate Chelating Agent," *Proc. Natl. Acad. Sci. USA*, 854025–4029, 1988.

Gansow, Otto A., Newer Approaches to the Radiolabeling of Monoclonal Antibodies by Use of Metal Chelates. *Nucl. Med. Biol.*, 18(4):369–381, 1991.

Goldenberg and Griffiths, "Radioimmunotherapy of Cancer: Arming the Missiles," *J. Nucl. Med.*, 33(6):1110–1112, 1992.

Goldrosen et al., "Biodistribution, Pharmacokinetic, and Imaging Studies with $^{186}$Re–labeled NR–LU–10 Whole Antibody in LS174T Colonic Tumor–bearing Mice," *Canc. Res.*, 50:7973–7978, 1990.

Granowska et al., "Radiolabeled Stripped Mucin, SM3, Monoclonal Antibody for Immunoscintigraphy of Ovarian Tumours," *Int. J. Biolog. Markers*, 5(2):89–96, 1990.

Granowska et al., "Diagnostic Evaluation of $^{111}$In and $^{99m}$Tc Radiolabelled Monoclonal Antibodies in Ovarian and Colorectal Cancer: Correlations with Surgery," *Nucl. Med. Biol.*, 18(4):413–424, 1991.

Griffiths et al., "Radiolabeling of Monoclonal Antibodies and Fragments with Technetium and Rhenium," *Bioconjugate Chem.*, 3(2):91–99, 1992.

Griffiths et al., "Direct Radiolabeling of Monoclonal Antibodies with Generator–produced Rhenium–188 for Radioimmunotherapy: Labeling and Animal Biodistribution Studies," *Canc. Res.*, 51:4594–4602, 1991.

Hansen et al., "Preclinical Evaluation of an Instant $^{99m}$Tc–labeling Kit for Antibody Imaging," *Canc. Res. (Suppl.)*, 50:794s–798s, 1990.

Hawkins et al., "Resistance of Direct Tc–99m–Protein Bond to Transchelation," *Antibody, Immunoconjugates, Radiopharm.*, 3(1):17–25, 1990.

Hnatowich et al., "Concerning the Labeling of DTPA–Coupled Proteins with Tc–99m." *J. Nucl. Med.*, 24(6):544–546, 1982.

Hosotani et al., "Design of Bifunctional Radiopharmaceutical for the Development of $^{99m}$Tc Complexes for Myocardial Imaging Agents," *Nucl. Med. Biol.*, 13(6):603–609, 1986.

Hotze et al., "Technetium–99m–Labeled Anti–Granulocyte Antibodies in Suspected Bone Infections," *J. Nucl. Med.*, 33(4):526–531, 1992.

Joiris et al., "A New Method for Labelling of Monoclonal Antibodies and their Fragments with Technetium–99m," *Nucl. Med. Biol.*, 18(3):353–356, 1991.

Khaw et al., "Technetium–99m Labeling of Antibodies to Cardiac Myosin Fab and to Human Fibrinogen," *J. Nucl. Med.*, 23(11):1011–1019, 1982.

Lanteigne and Hnatowich, "The Labeling of DTPA–coupled Proteins with $^{99m}$–Tc," *Int. J. Appl. Radiat. Isol.*, 35(7):617–621, 1984.

Lever et al., "Synthesis of a Novel Bifunctional Chelate Designed for labeling Proteins with Technetium–99m," *Tetrahedron Lett.*, 29(26):3219–3222, 1988.

Lind et al., "Anti–Carcinoembryonic Antigen Immunoscintigraphy (Technetium–99m–Monoclonal Antibody BW 431/26) and Serum CEA Levels in Patients with Suspected Primary and Recurrent Colorectal Carcinoma," *J. Nucl. Med.*, 32(7):1319–1325, 1991.

Linder et al., "Technetium Labeling of Monoclonal Antibodies with Functionalized BATOs. 1. TcCl(DMG₃PITC)," *Bioconjugate Chem.*, 2:160–170, 1991.

Mather and Ellison, "Reduction–Mediated Technetium–99m Labeling of Monoclonal Antibodies," *J. Nucl. Med.*, 31(5):692–697, 1990.

Morrison et al., "Current Diagnostic Efficacy of Tc–99m–Labeled Antitumor Antibodies," *Radioimmunoimaging and Radioimmunotherapy*, pp. 369–383, 1983.

Morrison et al., "Radioimmunoimaging with $^{99m}$Tc Monoclonal Antibodies: Clinical Studies," *Int. J. Nucl. Med. Biol.*, 11(2):184–188, 1984.

Mukherjee et al., "Cysteine a Chelating Moiety for Synthesis of Technetium–99m Radiopharmaceuticals—Part I. Benzoyl Cysteine and Derivatives," *Nucl. Med. Biol.*, 16(7):715–720, 1989.

Najafi et al., "The Evaluation of $^{186}$Re–labeled Antibodies Using N₂S₄ Chelate *In Vitro* and *In Vivo* Using Tumor–Bearing Nude Mice," *Nucl. Med. Biol.* 19(2):205–212, 1992.

Ohmomo et al., "New Conformationally Restricted $^{99m}$Tc N₂S₂ Complexes as Myocardial Perfusion Imaging Agents," *J. Med. Chem.*, 35:157–162, 1992.

Pak et al., "An Instant Kit Method for Labeling Antimyosin Fab' with Technetium–99m: Evaluation in an Experimental Myocardial Infarct Model," *J. Nucl. Med.*, 33(1):144–149, 1992.

Pak et al., "Evaluation of the 323/A3 Monoclonal Antibody and the Use of Technetium–99m–labeled 323/A3 Fab' for the Detection of Pan Adenocarcinoma," *Nucl. Med. Biol.*, 18(5):483–497, 1991.

Pettit et al., "Improved Protein Labeling By Stannous Tartrate Reduction of Pertechnetate," *J. Nucl. Med.*, 21:59–62, 1980.

Quadri and Wessels, "Radiolabeled Biomolecules with $^{186}$Re: Potential for Radioimmunotherapy," *Nucl. Med. Biol.*, 13(4):447–451, 1986.

Rhodes et al., "$^{99m}$Tc–Labeling and Acceptance Testing of Radiolabeled Antibodies and Antibody Fragments," *Tumor Imaging*, pp. 111–123, 1990.

Rhodes and Martinez–Duncker, "Direct Labeling of Antibodies with Tc–99m," *Radioimmunoimaging*, pp. 50–53, Mar. 1990.

Rhodes and Burchiel, "Radiolabeling of Antibodies with Technetium–99m," *Radioimmunoimaging and Radioimmunotherapy*, pp. 208–222, 1983.

Salk et al., "Technetium–Labeled Monoclonal Antibodies for Imaging Metastatic Melanoma: Results of a Multicenter Clinical Study," *Seminars in Oncology*, 15(6):608–618, 1988.

Schroff et al., "Rhenium–186 Labeled Antibody in Patients with Cancer: Report of a Pilot Phase I Study," *Antibody, Immunoconjugates, Radiopharm.*, 3(2):99–111, 1990.

Shimura et al., "Radioimmunodetection of Human Colon Cancer Using $^{99m}$Tc MDP–MoAb–A7 in Mice," *Nucl. Med. Biol.*, 18(1):105–109, 1992.

Srivastava and Mease, "Progress in Research on Ligands, Nuclides and Techniques for Labeling Monoclonal Antibodies," *Nucl. Med. Biol.*, 18(6): 589–603, 1991.

Stepniak–Biniakiewicz et al., "A New, General Synthetic Route to Multidentate N,S Ligands for use in Technetium–99m Radiopharmaceuticals. Preparation of Diamido Disulfer, Diamino Dithiol, and Tripodal N₃S₃ Prototypes. Comparative Biodistributions of [$^{99m}$Tc$^{v}$O–DADS] Analogues Which Contain 5,5,5–and 5,7, 5–Membered Chelate Ring Systems," *J. Med. Chem.*, 35:274–279, 1992.

van Dongen et al., "Radioimmunoscintigraphy of Head and Neck Cancer Using $^{99m}$Tc labeled Monoclonal Antibody. E48 F(ab')," *Canc. Res.*, 52:2569–2574, 1992.

Washburn, Lee C., "Radiochemistry of Monoclonal Antibody Labeling," *new Trends in Radiopharmaceutical Synthesis, Quality Assurance and Regulatory Control*, pp.183–191, 1991.

Wong and Huang, "Labeling of Human Immune Gamma Globulin with $^{99m}$Tc," *Int. J. Appl. Radiat. Isotopes*, 28:719–722, 1977.

Weber et al., "Enchanced Kidney Clearance with an Ester––Linked $^{99m}$Tc–Radiolabeled Antibody Fab'–Chelator Conjugate," *Bioconjugate Chem.*, 1:431–437, 1990.

Zimmer et al., "Pharmacokinetics of $^{99m}$Tc(Sn)—and $^{131}$I–labeled Anti–Carcinoembryonic Antigen Monoclonal Antibody Fragments in Nude Mice," *Canc. Res.*, 47:1691–1694, 1987.

Bhargava et al., "Hydroxamic Acid Derivatives as Ligands for Technetium–99m Labeled Radiopharmaceuticals," Abstract No. 122, 194th National Meeting of the American Chemical Society, Division of Nuclear Chemistry & Technology, Aug. 30, 1987, New Orleans, Louisiana.

Collection of Abstracts from the Proceedings of the 38th Annual Meeting, Poster Sessions *The Journal of Nuclear Medicine*, 33(6) pp. 988, 989, 1102 and 1033, 1992.

Dialog Search Report dated Aug. 27, 1992.

HYDROXAMIC ACID-BASED BIFUNCTIONAL CHELATING COMPOUNDS

This application is a continuation of Ser. No. 7/941,986, filed Sep. 8, 1992, now abandoned.

BACKGROUND OF THE INVENTION

1. Field of the Invention

This invention relates to the field of linkers attaching ion-chelating groups to biologic molecules such as proteins or nucleic acids as well as tissues such as blood cells. More particularly, the present invention relates to hydroxamic acid-based bifunctional chelating agents (BCAs) that are designed to link pharmaceutically useful ions, such as radioactive or paramagnetic ions, to, for example, monoclonal antibodies that will direct the ion to a desired target tissue.

2. Description of the Related Art

Due to their high antigen specificity, monoclonal antibodies (mAbs) constitute an increasingly important class of agents in both diagnosis and therapy of cancer (1). One of the main strategies in their utilization in the treatment of cancer is the preparation of radiolabeled mAbs (2,3). Both direct and indirect techniques have been used for radiolabeling of these proteins. The direct method involves the attachment of the radioactive element onto an appropriate amino acid side chain of the polypeptide backbone of the antibody (4,5). An example of this method is radioiodination of antibodies through their tyrosine residues (4). In the indirect method, on the other hand, the radionuclide is attached to the protein through a linking molecule (6). In recent years, the latter method has gained more attention due to, particularly, a number of problems involved with directly radioiodinated mAbs (7) and growing interest in radioactive metals.

The indirect method offers advantages of allowing preparation of the underlying construct in accordance with the structural requirements, the most important of which are the chelating power of the ligand, in vivo stability of the labeled conjugate and the normal tissue clearance (NTC). All of these criteria are a function of the structural design and manipulation of the reagents employed for preparation of the construct, but have as yet to be optimized. Generally speaking, the linkers used in the indirect method are bifunctional chelating agents (BCAs), which possess a group capable of binding a radioactive element (the chelating function) and one that binds to the protein (the conjugating function) (8). A number of BCAs, with different types of functionalities, have been synthesized and used in the labeling of mAbs. More well-known and frequently used examples are diethylenetriaminepentaacetic acid, DTPA, and its derivatives (9) and mercaptoacetylglycylglycyl-gamma-aminobutyrate, $MAG_2$-GABA (10) for radiolabeling of mAbs. Although promising results have been achieved with some of these compounds, they nevertheless suffer from significant drawbacks, including difficult and long synthetic procedures, limitations in applicability to a wider range of radioactive metals and unfavorable normal tissue clearances.

Hydroxamic acids have been known for some time for their chelating ability towards metallic nuclides (11–14), and have been mentioned as possible chelators in the context of radiopharmaceuticals for technetium-99m labeling (Bhargava, K. K. et al. (1987), Abstract, 194th National Meeting of the American Chemical Society, Division of Nuclear Chemistry and Technology, Albert Einstein College of Medicine, Bronx, N.Y.). Unfortunately, this report was quite limited, and failed to suggest structures that would be useful to chelate ions to monoclonal antibodies or other proteins. For example, the hydroxamic acids reported by this article are not capable of being conjugated to proteins or peptides, through known chemistries, in such a way that the hydroxamic acid functions are left intact when the conjugation process is carried out. This is due to the reactivity of the free hydroxamate groups that are present on these structures. Thus, the structures of Bhargava et al. are not capable of being successfully attached to proteins or nucleic acids in the form disclosed by the present invention. A similar situation exists with compounds suggested by another group of investigators and included herein by reference (15).

Even though some improvements have been made in existing radiopharmaceuticals, there is nevertheless a significant need for advances that would address one or more of the disadvantages discussed above. In particular, there is a need for bifunctional chelators having improved pharmacologic characteristics of in vivo stability and NTC, as well as good protein attachment and chelator features. There is, for example, a particular need for the bifunctional chelators for use in both imaging and treatment that may be prepared well in advance of their use, and yet provide a stable complex with the selected ion.

SUMMARY OF THE INVENTION

The present invention addresses these and other disadvantages in the art through the use of hydroxamic acid-based chelators for the attachment of metal ions to targeting proteins such as monoclonal antibodies. The invention arises out of the inventors' discovery that hydroxamic acid-based chelators offer particular advantages, including wide range applicability (i.e., to more than one or two metal ions), good stability features and even having the potential of being used as a kit for patient imaging or therapy. Generally speaking, the linkers of the invention will include both hydroxamic acid chelator moieties and a protein attachment or conjugating moiety. Preferred bifunctional chelators of the present invention may further include a linker region positioned between the protein conjugation group and the hydroxamic acid function. Linker regions to separate the two functions may ensure the independent actions of each function and incorporation of special structural features for improved properties (e.g., blood or other normal tissue clearances).

Thus, preferred bifunctional chelators will have a general formula of

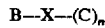

wherein B is the protein binding or attachment moiety, C is the hydroxamic acid moiety, X is the linker region and n=1, 2, 3, etc.

The "B" region of the foregoing general formula is a chemical moiety adapted for attaching the linker construct to the protein, monoclonal antibody or other molecules of interest. Furthermore, part $(C)_n$ may be attached to the linker X at different loci rather than at the same point.

Preferred protein attachment moieties in molecules of the type disclosed in this invention will sometimes comprise carboxylic acid or aldehyde functions. Carboxylic acid functions will form stable, covalent bonds with functional groups prevalent on proteins and nucleic acids, such as a free amino or thiol, through processes of aminolysis and thiolysis, respectively. The resultant amide or thiol-ester are preferred covalent bonds in that they are stable and are capable of being formed under relatively mild conditions that will not denature proteins or other molecules attached to the hydroxamic acid function. Moreover, functions such as these are stable under conditions generally found in the body to the extent suitable for treatment of the patients.

In other preferred embodiments, aldehyde groups will perform the conjugating function. The use of aldehyde groups may be expected to present some advantages over carboxylic acid groups since concerns exist as to the possibility of interference of the free hydroxamate functions with the chemistry used to conjugate BCAs to the protein, monoclonal antibody, or molecule of interest with active ester coupling of carboxylic acids. To prevent this interference, the O-benzyl groups which protect the hydroxamic acid functions are removed after conjugation when carboxylic acid conjugation is employed. Good results have been obtained using this method, however, concerns over the efficacy of the O-benzyl deprotection step remain, and quantitative removal of these groups, which ensure availability of all of the chelating hydroxamate functions for radiolabeling would be desirable. Use of aldehyde groups as the conjugating function will allow for deprotection prior to conjugation to the protein.

The feasibility of using aldehyde groups for the conjugation has been demonstrated in studies involving desferrioxamine (DFO). DFO has been conjugated to a number of proteins through a two-step process. In this procedure the free —$NH_2$ group of DFO is first coupled to one of the aldehyde (—CHO) groups of glutaraldehyde through a reductive alkylation reaction. The other —CHO function of the attached glutaraldehyde is then conjugated to the protein molecule through a second amination step. Through this technique, high yields of conjugation with preserved conjugate immunoreactivities have been reported. These studies prove that free hydroxamate acid functions can co-exist with aldehyde groups on the same molecule and not interfere with the reductive alkylation chemistry used for the conjugation.

Based on the above findings, the inventors propose preferred embodiments of the BCAs in which an aldehyde group will serve as the conjugation function. O-benzyl protecting groups of this molecule can be removed before the ligand is attached to any macromolecule (e.g., a mAb). Therefore, potential problems during deprotection are avoided, and quantitative O-benzyl deprotection can be assured.

An important aspect of the invention is the use of metal ion chelating structures that include one or more hydroxamic acid or hydroxamide functions. Hydroxamic acid is a functional structure that include both a nitrogen and an oxygen as electron donors, and can be readily synthesized by reaction of an ester or a nitrile with hydroxylamine, or by the reaction of a protected hydroxylamine and a carboxylic acid. Due to its high electron density, hydroxamic acid chelators form strong complexes with a number of metal ions. While some chelators may include only a single hydroxamic acid moiety, preferred chelators will incorporate two, three or more such functions, with improved binding and complex stability characteristics.

The hydroxamic acid function that is employed can take a variety of structures. An exemplary structure is trisuccin (1, FIG. 1) as shown below:

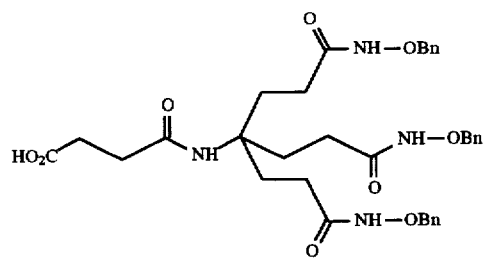

It will be appreciated that the subsections B, C and X are shown in the foregoing diagram. Of course, if carboxylic acid conjugation is employed, protected hydroxamic acid functions will be liberated after attachment of the molecules to, e.g., an antibody, by, e.g., catalytic hydrogenation (see below).

Part X is the linker region, which acts to attach the protein binding functions to the hydroxamic acid chelator. The structure of the linker is not particularly crucial to the practice of the broad concept of the invention, so long as the linker is pharmacologically acceptable and biologically non-reactive when prepared for use. However, numerous structural variations in the linker are possible, and these variations result in distinct advantages in some of the preferred embodiments of the invention. These variations are made according to structure-activity relationship (SAR) and structure-stability relationship (SSR) hypotheses.

Variations in the linker region may be of particular importance in influencing the functional characteristics of a BCA, such as metal chelating abilities, biodistribution and tumor-to-normal tissue activity ratios. This part of the molecule may also have a considerable effect on the catabolism of conjugates that have been introduced into a body and, consequentially their rate of clearance from normal tissues. Optimization of the structure of the linker region, based on experimental data accumulated during the course of animal studies, is possible.

Preferred linker regions will be esters, peptide and amide bonds. Linkers such as these are preferred in that they are inert to conjugation and radiolabeling conditions and may aid in the final tissue clearance. However, the inventors contemplate that other linker regions such as sulfides and disulfides can be employed where desired or appropriate. Generally, structures such as alkyl straight chains, with saturated structures, should be avoided due to their relative inertness towards metabolic processes which may result in their persistence in normal tissues and, as a result, long clearance periods. Structures with high molecular weights (e.g., greater than 700) should be avoided because of immunogenicity problems. The linker portion of the molecule may be constructed by starting with compounds from commercial sources using techniques that will be apparent to those of skill in the art in light of the present disclosure.

One group of preferred linkers includes those that comprise esters. It has been reported that esters are readily metabolized in the body and a good rate of organ cleavage of ester-containing BCAs has been reported (16). Due to their ease of catabolism, readily metabolizable structures are expected to exhibit faster in vivo clearance from such organs as the liver and kidneys. Although almost any ester-containing linker region could be expected to exhibit these benefits, some more preferred linkages are those containing carboxylic esters, since carboxylic esters have been shown to exhibit particularly good clearance (16).

Most preferred linkers containing carboxylic esters are 3-carboxypropyl N-[Tris[2-[[N-(benzyloxy)amino]

carbonyl]ethyl]-methyl]succinamate, (nicknamed-trisuccin, 3-carboxypropyl ester) and N,N-Bis[(N-hydroxylaminocarbonyl)methyl]-2-[2-(N-hydroxylaminocarbonyl)ethyl]glycine, formylmethyl ester.

Other preferred linkers are those which include a peptide bond. Like an ester bond, such a bond may be expected to facilitate radioisotope clearance. Of course, any peptide bond is expected to have some degree of utility in the present invention, but most preferably this would be an amino acid-amino acid bond.

The synthesis of bifunctional chelators in accordance with the invention will generally involve the preparation of "protected" hydroxamic acid functions to prevent them from interfering with other reactive intermediates during formation of the linker. In some embodiments, such as when the protein conjugation functions are carboxylic acid based, the hydroxamic acid functions will need to remain protected during attachment of the BCA to the protein. Generally speaking, hydroxamic acid moieties are protected by benzyl groups. The blocking group is removed by catalytic hydrogenation to unmask the active metal chelating function. An example is the removal of a benzyl protecting group by heterogeneous catalytic hydrogenation using a palladium and/or platinum on activated carbon catalyst. As stated above, the removal of the blocking group is usually done after the conjugation of the BCA to the protein if carboxylic acid group-based conjugation is used, but can be done prior to conjugation if the conjugation is aldehyde based.

A particularly preferred bifunctional chelating agent in accordance with the invention is termed "trisuccin" by the inventors, because of its structure which includes three hydroxamic acid functions with a succinic acid backbone. The chemical name of trisuccin is N-[tris(2-N-benzyloxyaminocarbonylethyl)] methylsuccinamic acid (see FIG. 1).

In general terms, trisuccin is prepared by coupling of an amino triester to monomethyl succinate through a reaction with DCC and HOBT. The tert-butyl ester groups of the resulting amide were removed with TFA to afford the tricarboxylic acid. The latter compound, upon complete removal of the solvent, is coupled to three equivalents of O-benzylhydroxylamine in a DCC/HOBT reaction. Base hydrolysis of the methyl ester deblocked the carboxyl terminus (the protein conjugating function) of the molecule.

There are a number of compounds related to trisuccin in their structure, which are prepared in a similar fashion to trisuccin, and are contemplated to be within the scope of the present invention. Examples include N,N-bis-(benzylhydroxylaminocarbonylmethyl) glycyl-glycine, and even its succinic acid derivatives, shown by structure 2 and 3 below:

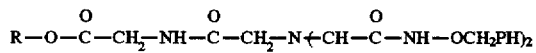

wherein "2", R=H, and in "3", R=CH$_2$—CH$_2$CO$_2$H

The synthesis of structures such as these involve substitution of the N-terminal hydrogens of glycylglycine, ethyl ether (prepared by coupling of BOC-glycine and glycine ethyl ester through the agency of DCC and HOBT), with benzyl bromoacetate and hydrolysis of the ethyl ester to give the B-region carbonyl group (compound 2). Compound 3 is then prepared from compound 2 by coupling of the latter with mono-tert-butyl succinate and final acidolysis of the tert-butyl group.

Another preferred embodiment of the present invention comprises BCAs with glutamic acid backbones. Such BCAs are anticipated to hold improved isotope-linking properties. One of the most preferred embodiments of these glutamic acid BCAs is N,N-Bis[(N-hydroxylaminocarbonyl)ethyl]-2-[2-(N-hydroxylaminocarbonyl)ethyl]glycine, formylmethyl ester. This molecule has the same number of hydroxamate functions (three) and, additionally, contains a tertiary nitrogen which may further enhance the chelatability of the whole ligand system, by a direct complexation between this nitrogen atom and the metal. Moreover, this compound also will accommodate, in its linker arm, a carboxylic ester moiety which should improve its in vivo clearance as discussed above.

In addition to open-chain compounds such as trisuccin and structure 31, N,N-Bis[(N-hydroxylaminocarbonyl) methyl]-2-[2-(N-hydroxylaminocarbonyl)ethyl]glycine, formylmethyl ester, the inventors contemplate that a variety of other structures may be employed that will exhibit the advantages of trisuccin. Examples include pyrrolidine derivatives, which are characterized as cyclic derivatives. An example of a pyrrolidine derivative is the compound below:

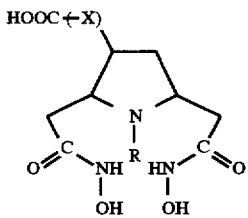

The "C" part in this compound is again a combination of hydroxamic acid functions, the "X" part is a linker consisting of alkyl esters, sulfoxides or sulfones, and the "B" part is either a carboxyl or an aldehyde group.

It is contemplated that bifunctional chelators of the present invention will find their greatest application in providing a means for attaching radioactive and paramagnetic metal ions to monoclonal antibodies having a selective binding affinity towards a particular cell or tissue type, such as anti-tumor antibodies. Such constructs take advantage of the specific targeting capabilities of monoclonal antibodies to direct the metal ligand to the targeted tissue or cell, thereby allowing its imaging or even destruction, depending on the specificity of the antibody, and the nature of the selected metal ligand (e.g., radioactive or not, type of radiation emission, etc.).

The antibody that is selected will, of course, depend on the intended application. Where one intends to employ the resultant conjugate for tumor imaging or therapy, one will select an antibody having specificity for the selected tumor. Examples include monoclonal antibodies such as CC49 and D612 (anticolorectal carcinoma) and 14G2a (antimelanoma). Of course, applicability of the invention is not limited to tumor imaging or treatment, and can be applied to carry any desired metal ligand to any targeted tissue so long as there is an appropriate targeting antibody available. Where therapy as opposed to imaging is contemplated, it will be appreciated that highly selective antibodies will be required for specific targeting of the tumors with radionuclides such as rhenium-186 and possibly such radioactive metals as copper-67 and yttrium-90. However, for imaging purposes, where paramagnetic or less cytotoxic ions are employed, the antibody need only be sufficiently selective to provide a useful image.

7

Figure 2:
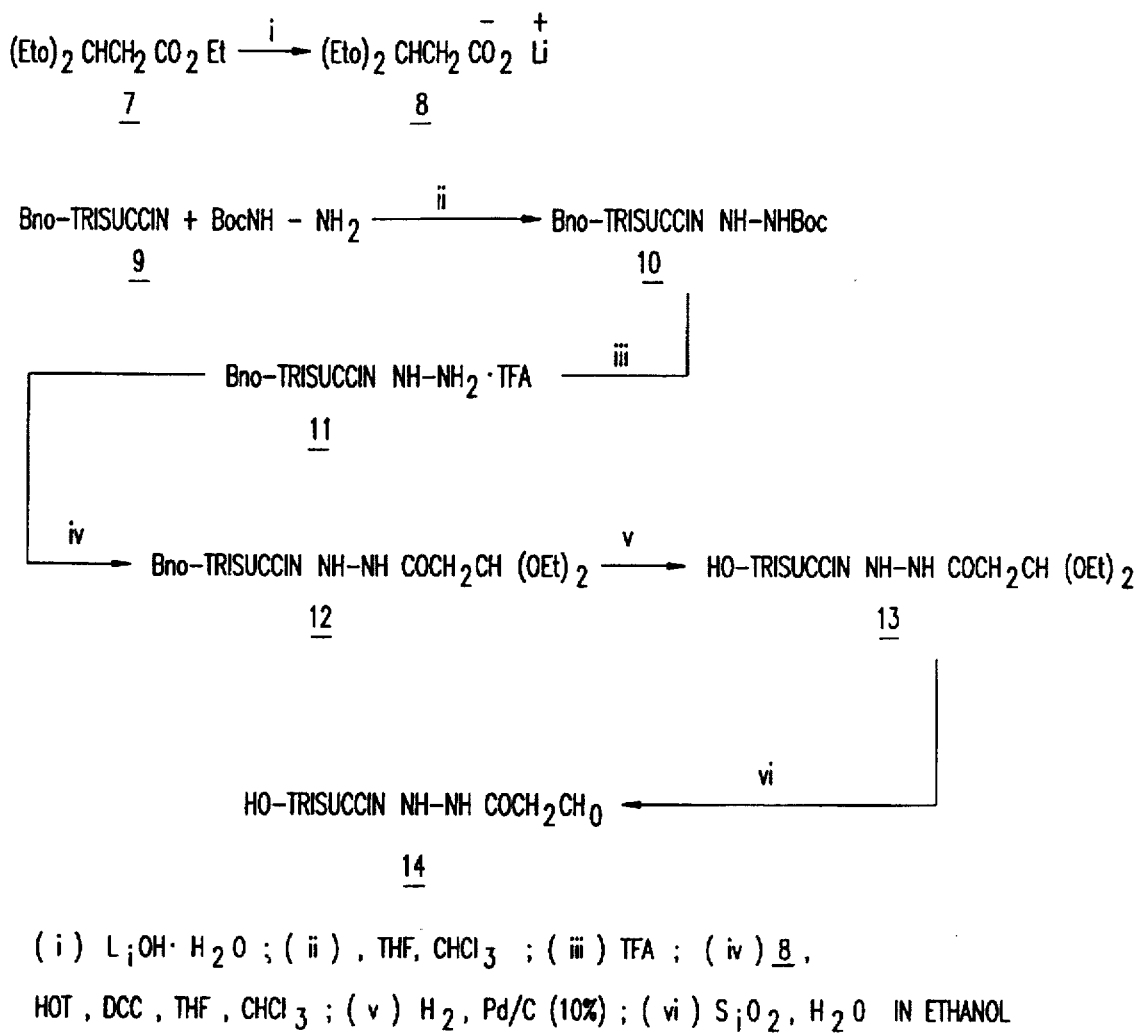

FIG. 2: Schematic representation of the synthesis of a trisuccin compound that has aldehyde instead of carboxylic acid protein conjugation functions.

Figure 3:
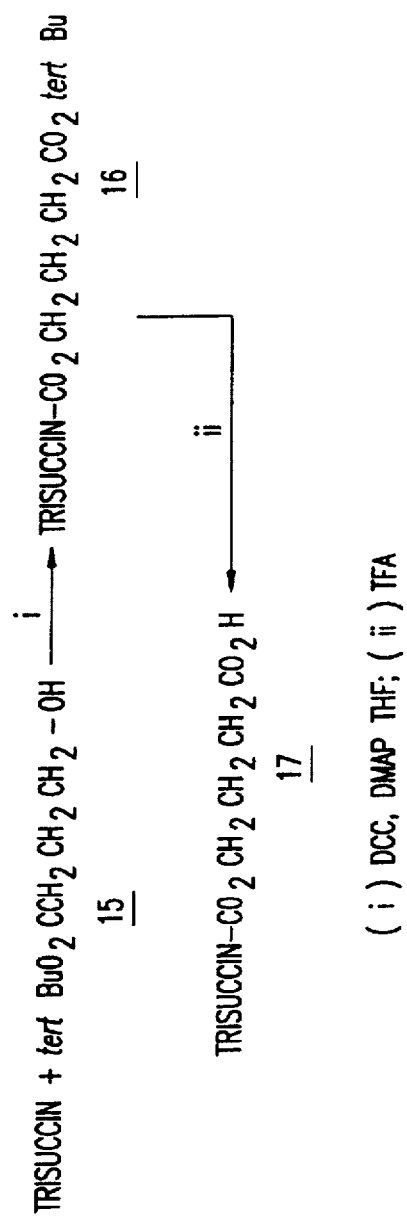

FIG. 3: Schematic representation of the synthesis of 3-carboxypropyl N-[Tris[2-[[N-(benzyloxy)amino] carbonyl]ethyl]-methyl]succinamate, a BCA with an ester in its linker region.

Figure 4:
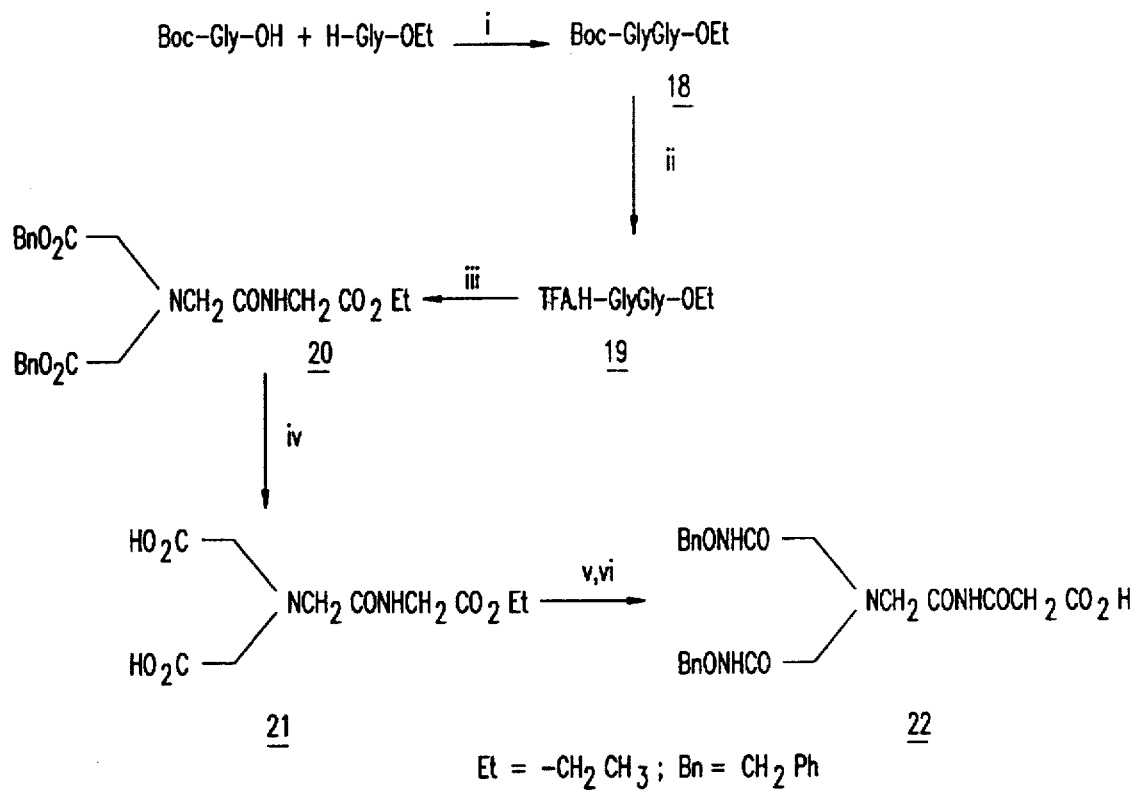

FIG. 4: Schematic representation of the synthesis of compound 22, N,N-bis-(benzylhydroxylaminocarbonylmethyl) glycylglycine, a BCA with a peptide bond in its linker region.

Figure 5:
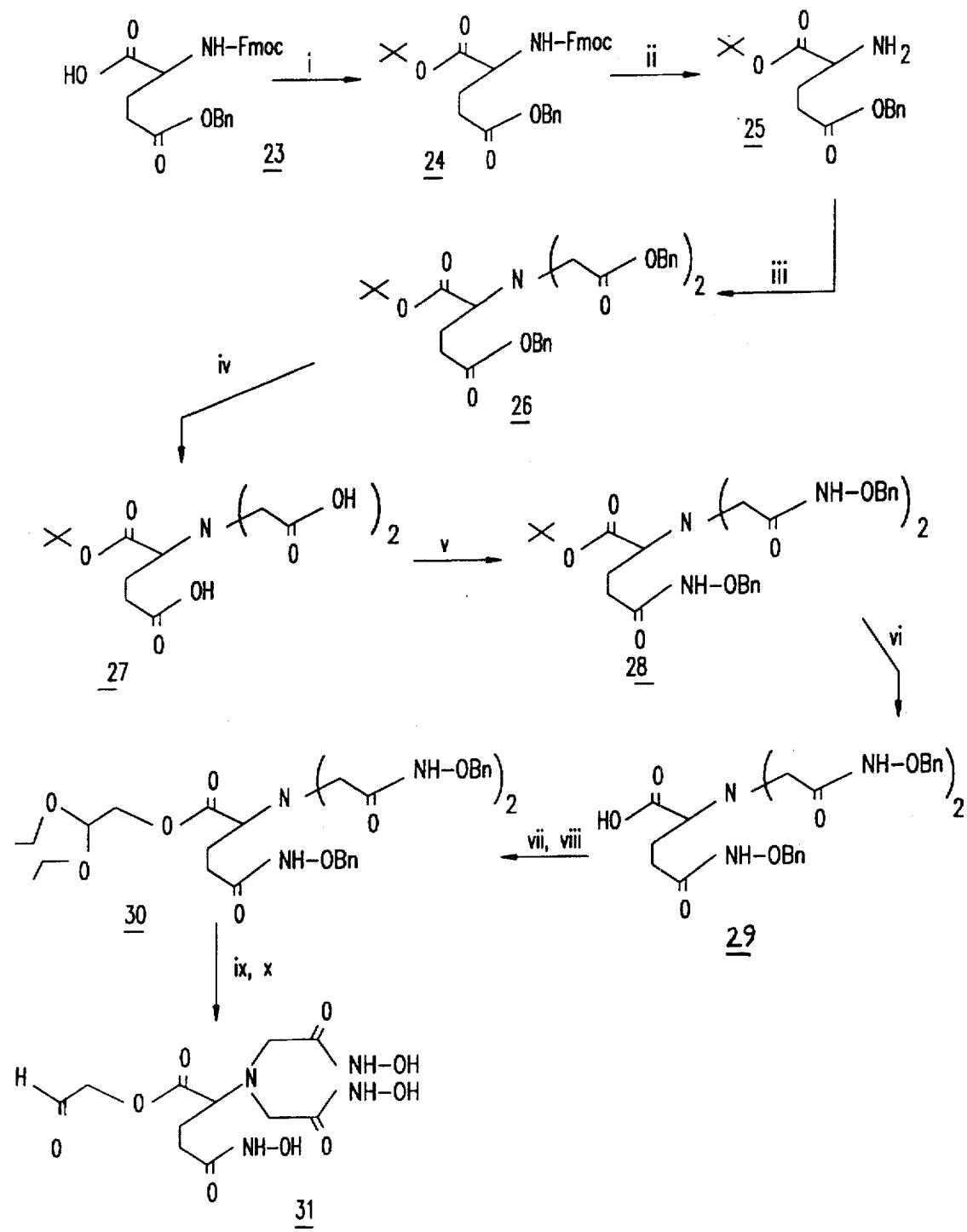

FIG. 5: Schematic representation of N,N-Bis[(N-hydroxylaminocarbonyl)methyl]-2-[2-(N hydroxylaminocarbonyl)methyl]glycine, formylmethyl ester, a novel hydroxamic BCA with a backbone formed out of glutamic acid groups.

Figure 6:
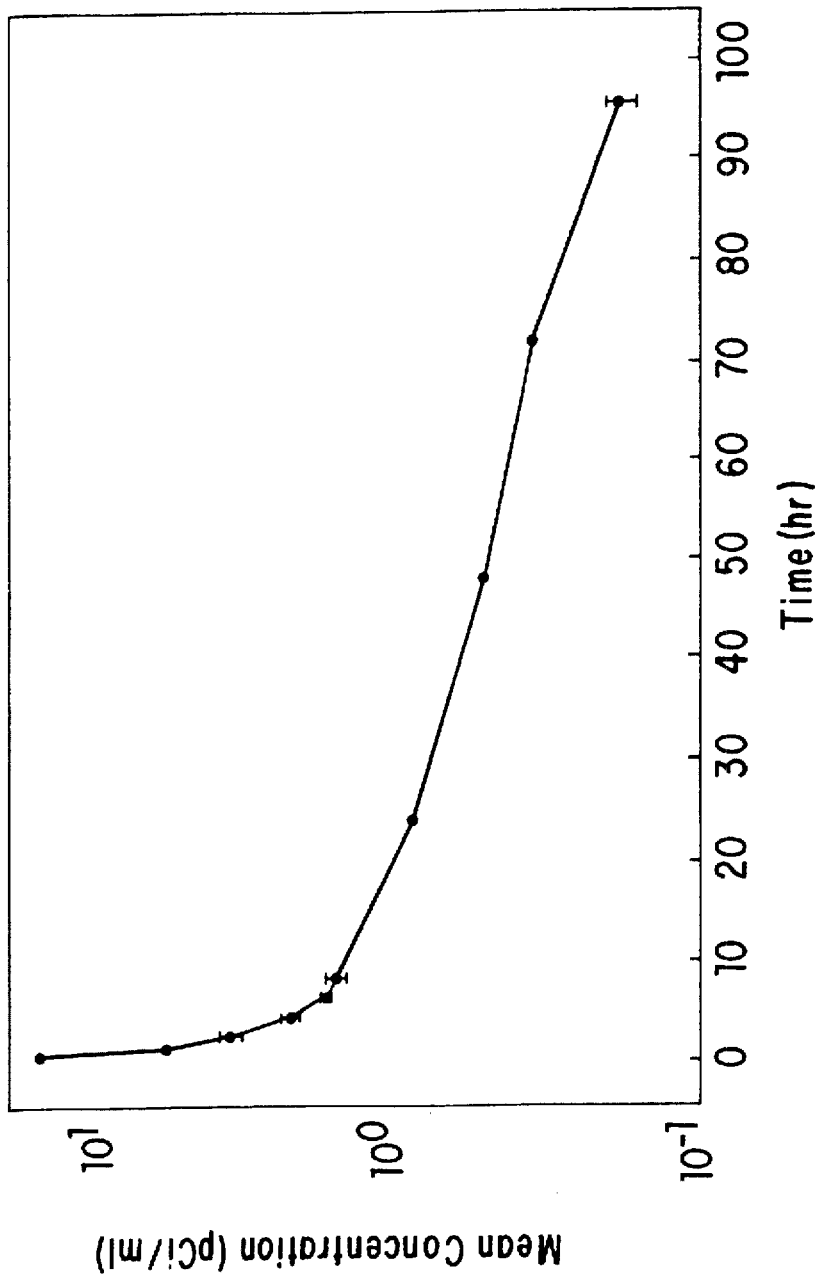

FIG. 6: Pharmacokinetic curve of $^{186}$Re labeled CC49 MAb in two rabbits receiving 100 μCi of $^{186}$Re-CC49.

DETAILED DESCRIPTION OF THE PREFERRED EMBODIMENTS

As part of a program aimed at the design and development of bifunctional chelating agents (BCAs) for radiometal labeling of monoclonal antibodies, the present inventors have developed a number of hydroxamic acid derivatives that have shown promise as a new class of BCAs that address at least one or more of the foregoing or other disadvantages in the art.

Preferred aspects of the invention involve the synthesis and mAb conjugation of N-[tris(2-N-benzyloxyaminocarbonylethyl)] methylsuccinamic acid, designated herein as trisuccin (1, FIG. I). Trisuccin has been conjugated to three different monoclonal antibodies and the subsequent conjugates radiolabeled with $^{99m}$Tc and/or $^{186}$Re.

Although the potential of monohydroxamic acids as chelating agents for metals had been reported (12,14), a particular advantage of the present invention involves BCAs having an increased number of hydroxamate functions, such as two or three. In initial conceptualization of the invention, the inventors proposed that an array of a number of hydroxamate groups positioned around a central carbon atom would create a cage-like assembly, capable of encapsulating a metallic nuclide, while maintaining a high degree of flexibility due to their existence as open-end chains.

Figure 1:
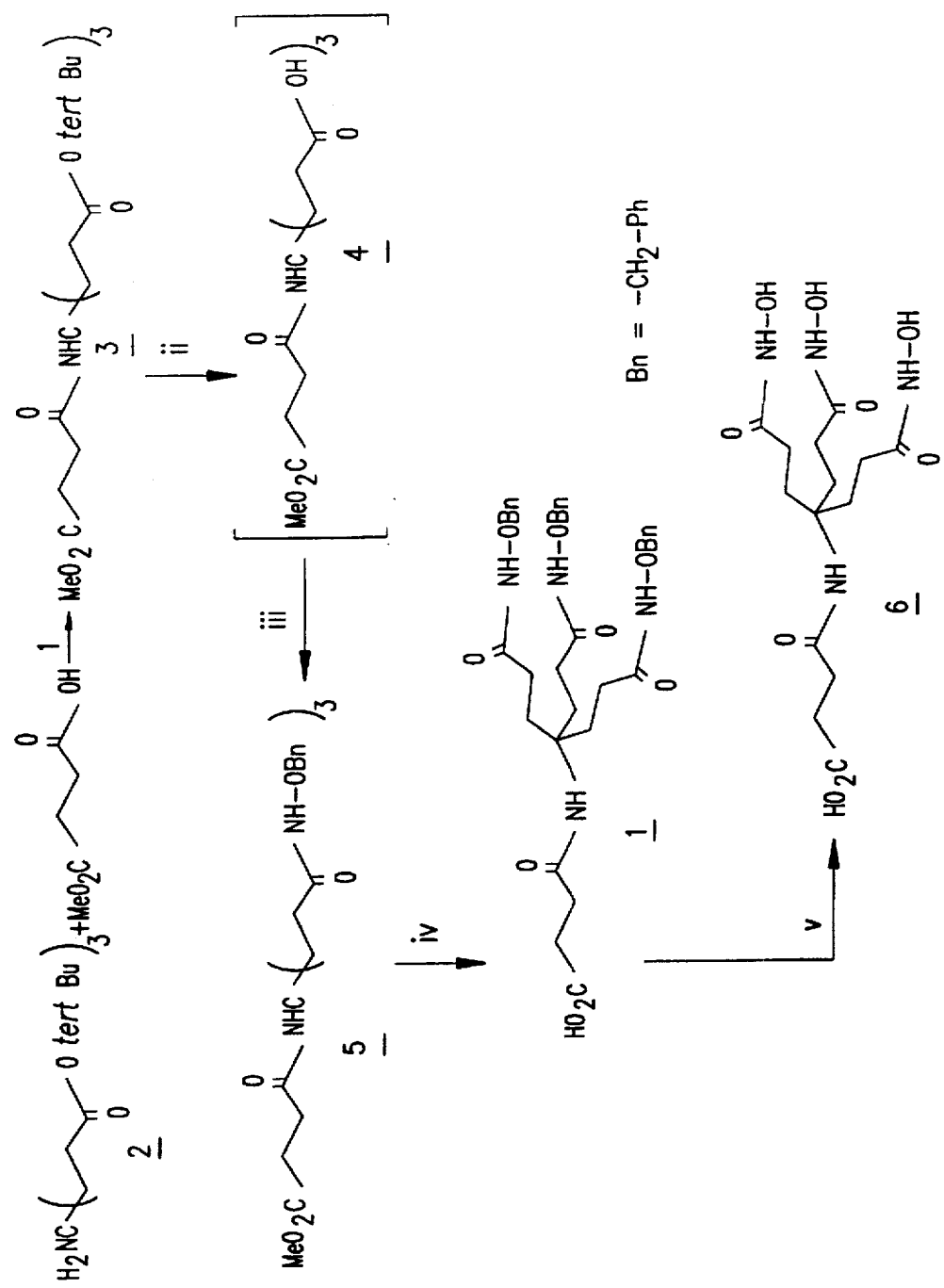
FIG. 1: Schematic representation of the synthesis of trisuccin.

The maximum number of hydroxamate moieties attached to a terminal Sp$^3$ carbon, i.e., three, was considered for this compound. The conjugating function, on the other hand, would strategically be placed at the opposite end of the molecule to minimize any interference in the independent functioning of each group. Therefore, the synthesis of the target compound was started with the aminotriester 2 (17) as shown in FIG. 1. This amine was coupled to monomethyl succinate through a reaction with DCC (18) and HOBT (19). The tert-butyl ester groups of the resulting amide 3 were removed with TFA to afford the tricarboxylic acid 4. The latter compound, upon complete removal of the solvent, was coupled to three equivalents of O-benzylhydroxylamine in a DCC/HOBT reaction to form 5. Base hydrolysis of the methyl ester 5 deblocked the carboxyl terminus (the protein-conjugating function) of the molecule.

8

EXAMPLE I

SYNTHESIS OF TRISUCCIN

A. Materials and Methods

1. Miscellaneous Procedures

All reagents and solvents may be used as received without further purification. Aminotriester 2 (17) was a gift from Dr. G. R. Newkome, University of South Florida, Tampa, FL.

Melting points are uncorrected and may be measured in open-end capillaries on an Electrothermal Model 9100 apparatus. $^1$H NMR spectra may be recorded on a Bruker WH400 at 400 MHz. Infrared spectra may be recorded on a Perkin Elmer-1600 FTIR spectrometer. Mass spectra may be determined by either a Varian MAT-311A (FAB Mode) in a nitrobenzyl alcohol matrix or a Finnigan TSQ-700/ESI (electrospray ionization, MS and MS/MS modes).

Column chromatographies may be carried out using silica gel 60 (EM Science, Gibbstown, NJ) and HPLC-grade solvents. Thin-layer chromatography (TLC) may be done on Whatman glass-backed silica gel plates, for example, 2.5 cm×7.5 cm, coating thickness 250 pm, 60A, 254 nm. Solvents for TLC may be mixed for example, on a V/V scale as follows: (A) 2-propanol: hexane: chloroform, 5:30:65; (B) ethyl acetate:chloroform, 25:75; (C) methanol:chloroform, 10:90; (D) acetic acid: methanol: chloroform, 3:20:77; (E) 2-propanol: chloroform, 15:85.

2. Preparation of Methyl N-[tris(2-tert-Butyloxycarbonylethyl)] Methylsuccinamate, 3.

The synthesis of Trisuccin is diagramed in FIG. 1, all numbers of products or intermediates in this and other synthesis schemes in the patent refer to structures in the relevant figure.

To a solution of monomethyl succinate (0.414 g, 3.14 mmol) in THF (8 mL), at 0° C. and under argon, was added a solution of HOBT (0.42 g, 3.12 mmol) followed by the addition of the aminotriester 2 (1.3 g, 3.12 mmol) in 10 mL of chloroform. The solution of DCC (0.68 g, 3.3 mmol) was added dropwise and within 10 min. The flask was then sealed and the reaction was allowed to stir under argon overnight, with gradual warming from 0° C. to room temperature. The solid precipitate was separated by vacuum filtration and the filtrate was concentrated to an oil in vacuum. The oil was redissolved in ethyl acetate (60 mL) and more precipitate was filtered off. The filtrate was washed, successively, with 15 mL each of water (1X), 10% citric acid solution (3X), water (2X), 10% sodium bicarbonate (3X), water (2X) and brine (1X) and dried over anhydrous magnesium sulfate powder.

Distillation of the solvent afforded a solid which was purified by column chromatography on silica gel with 50:50 (V/V), hexane:chloroform as the eluting solvent. A white solid powder (1.6 g, 96%) was obtained: mp 93.7°–95.5° C; TLC (I$_2$) R$_f$ 0.50 (A), R$_f$ 0.74 (B); FTIR (CHCl$_3$) 3345 (s, br), 3019 (s), 2950 (s), 1724 (s), 1662 (s); $^1$H NMR (CDCl$_3$) δ 1.45 (s, 27 H), 1.95 (t, J=8.32 Hz, 6 H), 2.20 (t, J=8.32, 6 H), 2.40 (t, J=7.28 Hz, 2 H), 2.64 (t, J=7.28 Hz, 2 H), 3.69 (s, 3 H); MS: m/e 530 (M+H)+; MS/MS:m/e 530 (M+H)+ .Anal.Calcd. for C$_{27}$H$_{47}$NO$_9$: C, 61.22; H, 8.94; N, 2.64. Found: 61.18; 8.99; 2.66.

3. Methyl N- [tris (2-N-Benzyioxyamino-carbonylethyl)] Methylsuccinamate, 5.

Trifluoroacetic acid (15 mL) was added to 3 (1.5 g, 2.8 mmol) under argon and at room temperature. The solution was allowed to stand at room temperature for 5 h and at 4° C. overnight. The solvent was distilled in vacuum and 15 mL each of chloroform, benzene, methanol and dry THF were successively distilled from the residue. The oily product was triturated with anhydrous ether and used directly in the next step. To the mixture of the tricarboxylic acid 4 (0.97 g, 2.7 mmol), HOBT (1.1 g, 8.1 mmol) and O-benzylhydroxylamine hydrochloride (1.31 g, 8.2 mmol) in THF (25 mL), at 0° C. and under argon, was added a solution of DCC (1.84 g, 8.9 mmol) within 3 min. A solution of DIEEA (1.1 g, 8.5 mmol) in 5 mL of THF was immediately added. The reaction mixture was stirred under argon for 48 h and filtered through a plug of celite.

Distillation of the solvent in vacuum afforded a light brown oil, which was redissolved in chloroform and washed with citric acid/sodium bicarbonate solutions, as described in the previous procedure, followed by flash chromatography on silica gel (25 g, 2 cm×15 cm column) using chloroform and a 0–5% methanol gradient to yield 0.74 g (41%) of 5 as a highly viscous oil. TLC, $R_f$ (A) 0.17, $R_f$ (C) 0.28; FTIR (CHCl$_3$) 3289 (s, br), 3225 (s, br), 3018 (s), 1750 (s), 1670 (s); NMR (CDCl$_3$) δ 1.85 (t,J=5.0 Hz, 6 H), 2.00 (t,J=5.0 Hz, 6 H), 2.32 (t,J=5.0 Hz, 2 H), 2.50 (t, J =5.0 Hz, 2 H), 3.44 (s, 3 H), 4.78 (s, 6 H), 7.32 (s, 15 H); MS: m/e 677 (M+H)+.

4. N-[tris(2-N-Benzyloxyaminocarbonyl-ethyl)] Methylsuccinamic Acid, 1 (Trisuccin)

To the solution of the methyl ester 5 (0.61 g, 0.9 mmol) in THF (5 mL) was added under an argon atmosphere, a solution of LiOH.·H$_2$O (0.042 g, 1 mmol) in water (1 mL). A second portion of lithium hydroxide (0.84 g, 2 mmol) in 1.2 mL of water was added after 2 h and the reaction mixture was incubated at room temperature overnight. A TLC of the reaction showed no starting ester. The solvent was distilled in vacuum at slightly below room temperature. Water (20 mL) was added and the solution was extracted with 15 mL of ether, followed by addition of HCl to pH 1.5–2, at 5° C. The precipitated product was extracted with ethyl acetate. The combined extracts were washed with water (2X) and brine (1X) and were dried over anhydrous magnesium sulfate.

Distillation of the solvent afforded 0.42 g (70%) of the product: TLC, $R_f$ 0.62 (D), 0.11 (E); FTIR (CHCl$_3$) 3475 (s, br), 3019 (s), 1675 (s), 1660 (s); $^1$H NMR (DMSO d$_6$) δ 1.77 (m, 6 H), 1.89 (m, 6 H), 2.33 (m, 2 H), 2.40 (m, 2 H), 4.76 (s, 6 H), 7.38 (m, 15 H); MS: m/e 663 (M+H)$^+$; MS/MS: m/e 663 (M+H6)$^+$.

5. N-[Tris[2-[(N-hydroxyamino)carbonyl]ethyl]-methyl] succinamic Acid, 6 (Deprotected Trisuccin)

The benzyl groups that protect the hydroxamic acid functions of trisuccin may be removed as follows to result in deprotected trisuccin (N-[Tris[2-[(N-hydroxyamino) carbonyl]ethyl]-methyl]succinamic Acid, 6). The protected hydroxamic derivative 1 (0.20 g, 0.3 mmol) in 95% ethanol (5 mL) was hydrogenated with 0.2 g of palladium on carbon (10%) at 20 psi and room temperature. The reaction progress was followed by TLC, which showed no starting material after 75 min. After an additional 45 min, the catalyst was separated by filtration through a plug of Celite and the solution was concentrated to 0.5 mL. The product was precipitated from petroleum ether, filtered, and dried under argon. The solid product was redissolved in 1 mL of methanol and precipitated one more time from petroleum ether. Drying the white powder under argon afforded 0.08 g (67.6%) of the hydroxamic acid: TLC (I$_2$, FeCl$_3$) $R_f$ 0.26 (J), 0.84 (K); FTIR (KBr) 3214 (br, 3446), 1655 (br, s, shoulders 1723, 1711); $^1$H NMR (DMSO-d$_6$) δ 1.79 (m, 6 H), 1.86 (m, 6 H), 2.27 (m, 2 H), 2.85 (m, 2 H), 3.60 (br, multiabsorption peak in the 2.6–4.3 range), 7.32 (s, 1 H); MS m/e 393 (M+H)$^+$.

EXAMPLE II

SYNTHESIS OF A TRISUCCIN WITH ALDEHYDE CONJUGATING FUNCTIONS

Synthesis of a trisuccin molecule with aldehyde conjugating functions is accomplishable as shown in FIG. 2.

Trisuccin is coupled to tert-butyl carbazate through a DCC/HOBT reaction in the manner previously described to form product 10. The Boc group of the product is removed by TFA to afford the trifluoroacetic acid salt 11 of the hydrazine derivative. Commercially available ethyl 3,3-diethoxypropionate 7 is base-hydrolyzed by lithium hydroxide in a DMF/H$_2$0 solution (40:1,v/v) and the resulting lithium salt 8 is coupled to the trisuccin hydrazine product by DCC/HOBT to produce 12. Product 12 is then hydrogenated catalytically with Pd/C (10%) to remove the O-benzyl protecting groups 13 and finally treated with wet silica gel or an acid (TFA) to free the aldehyde function and produce a trihydroxamic acid 14. The trihydroxamic acid (14) can then be conjugated to the lysine residues of the protein.

EXAMPLE III

VARIATIONS IN LINKER REGIONS

1. Esters in Linker Regions

There are several ways to introduce ester groups into the linker region of BCAs. One is shown in FIG. 3. The result of the synthesis scheme of FIG. 3 is 3-carboxypropyl N-[Tris[2-[[N-(benzyloxy)amino]carbonyl]ethyl]-methyl] succinamate, (nicknamed, trisuccin, 3-carboxypropyl ester). Trisuccin is esterified with tert-butyl 4-hydroxybutyrate, through a known procedure (20), in tetrahydrofuran (THF). The product 16 is converted to trisuccin, 3-carboxypropyl ester 17 with trifluoroacetic acid (TFA). This modification incorporates an ester linkage into the molecule which may result in further improvements in its in vivo organ clearance, while the conjugation function is preserved. All of the synthesized intermediates and final products can be purified by normal- or reversed-phase chromatography, or by some other standard method (e.g., crystallization) when necessary, for structural proof and analysis. Each structure can be established by a variety of different means, i.e., NMR- and mass spectroscopies and microanalysis.

2. Peptide Bonds in Linker Regions

The synthesis of BCAs containing a peptide bond may result in facilitated radioisotope clearance, particularly from the liver and the kidneys. The synthesis of a particular BCA containing a Gly—Gly peptide bond is demonstrated in FIG. 4. The intermediate 19 is prepared by the synthesis of the dipeptide 18, through coupling of N-tert-butyloxycarbonylglycine and glycine, ethyl ester using DCC and HOBT as reagents. Deprotection of the dipeptide is carried out by TFA. The N, N-disubstitution of the glyglyOEt dipeptide by benzyl bromoacetate (BBA) is achieved in dimethylformamide (DMF), in the presence of potassium bicarbonate. Intermediate 20 is then deprotected by catalytic hydrogenation to the dicarboxilic acid 21. The product, N,N-bis-(O-benzylhydroxylaminocarbonylmethyl) glycylglycine 22, is then prepared by the bis-coupling of 21 with 2 equivalents of O-benzylhydroxylamine (DCC/HOBT) and subsequent removal of the ethyl ester by base hydrolysis.

EXAMPLE IV

SYNTHESIS OF GLUTAMIC ACID BASED BCAs

FIG. 5 details the synthesis of a glutamic acid based BCA, N,N-Bis[(N-hydroxylaminocarbonyl)methyl]-2-[2-(N-hydroxylaminocarbonyl)ethyl]glycine, formylmethyl ester 31. This synthesis is carried out starting with esterification of Fmoc-Glu(OBn)—OH (N-9-fluorenylmethyloxycarbonylglutamic acid, gamma-benzyl ester, 23, available from a commercial source) with tert-butyl alcohol and DCC in the presence of catalytic amounts of DMAP. The Fmoc group is removed from 24 by a solution of piperidine in DMF (27) and the resulting intermediate is reacted with two equivalents of benzyl bromoacetate in DMF in the presence of potassium bicarbonate at 50° C. The tribenzyl ester 26 is then hydrogenated with 10% palladium on carbon at room temperature in ethanol. The resulting tricarboxylic acid 27 is coupled to three equivalents of O-benzylhydroxylamine. The tert-butyl ester group of the structure 28 is removed by reaction with TFA and the sodium salt of the resulting acid 29 is esterified with bromoacetaldehyde diethylacetal in dry DMF. Compound 30 can be deblocked to the free ligand structure 31 by two successive deblocking steps with catalytic hydrogenation (Pd/C, 10%) and wet silica gel (21), respectively.

EXAMPLE V

MONOCLONAL ANTIBODY CONJUGATION

The antibody is dialyzed in a membrane with a molecular weight cutoff of 25000 kD, in 0.1 M carbonate buffer at pH 9.5. To the solution of trisuccin in dry dimethylsulfoxide (DMSO) is added an equimolar solution of 2,3,5,6-tetrafluorophenol (TFP-OH) in DMSO followed by addition of 1.2 molar equivalents of dicyclohexylcarbodiimide (DCC). The solution is incubated at room temperature for 1.5 hours and added to the precooled (−5° C.) solution of the antibody. The solution is allowed to stir at −5° C. to 10° C. for about 2 hours. The antibody solution, as an average scale, contains about 7 to 10 mg of protein per ml. In each run, two ml of this solution is used. Different molar ratios of trisuccin to antibody have been tried.

The conjugation reaction is quenched, at the end of the 2 hour period, with the addition of about 10 μl of a 1 M solution of glycine in 0.1 M carbonate buffer (pH 9.5). The resulting solution is then purified by dialysis against phosphate-buffered saline (DPBS) in a membrane with a molecular weight cut off of 1000, at 4° C. for 6–8 hours.

The solution of the antibody-ligand conjugate is then subjected to hydrogenolysis in the presence of about 16 mg of palladium on activated carbon (10%) and 4–6 mg of 5% platinum on sulfide carbon for 3 hours and a hydrogen pressure of about 10 psi in a Parr hydrogenation apparatus. The catalyst is finally separated by centrifugation.

EXAMPLE VI

RADIOLABELING OF BCA-CONJUGATED MONOCLONAL ANTIBODIES

1. $^{99m}$Tc labeling

To 500 μL solution of the conjugate of Example V is added a 2-hydroxyisobutyric acid (HIBA) and stannous chloride ($SnCl_2$) in water (HIBA, 30 mg, $SnCl_2$, 3 mg/$H_2O$, 3 ml) is added (20 μL) and the mixture is incubated at 38° C.

2. $^{186}$Re Labeling

The solution of sodium-[$^{186}$Re]perrhenate (2 mCi) is mixed with the HIBA/$SnCl_2$ solution (100 μL of a solution containing 100 mg HIBA, 3 mg of $SnCl_2$ in 3 mL $H_2O$) and heated at a temperature between 55°–65° C. After 2 hours the solution is cooled and the pH is raised to about pH 6.5–7 with 0.25 N sodium hydroxide solution. The solution of the antibody conjugate is then added (400 μL) and incubated at 40° C. for about 1 hour.

3. $^{67}$Cu Labeling

Labeling of BCAs with $^{67}$Cu can be accomplished using the following procedure. One-molar stock solutions of acetic acid and ammonium acetate are separately prepared in purified, metal-free water. Radiolabeling of the conjugates with this isotope is performed at 0.05 M, 0.1 M, 1.0 M, ammonium acetate buffers at pH 5.5. The 0.050 M, and 0.1 M buffers are made by 1:20 and 1:10 dilutions, respectively, of the stock solutions and addition of an appropriate volume of the acetic acid solution to the solution of the ammonium acetate solution (same concentrations) to result in a pH of 5.5.

In a typical radiolabeling method, 2 mCi of $^{67}$Cu (supplied as cupric chloride in hydrochloric acid) is added to 500 μL of the ammonium acetate buffer and stirred at room temperature for 5 min to complete equilibration. The solution of the conjugated antibody in DPBS (200 μL), at an average protein concentration of 4 mg/mL, is then added to the $^{67}$Cu-containing buffer and stirred at room temperature. At 15 min intervals, 20 μL aliquots of this solution will be injected into SE-HPLC to follow the reaction progress. This labeling reaction can be repeated at higher incubation temperatures of 35° C. and 45° C. in order to optimize the labeling.

EXAMPLE VII

IMMUNOREACTIVITY AND STABILITY STUDIES

The binding activity of radiolabeled CC49 and control 14G2a antibody are measured by determining the percent absorption of labeled antibody to colon carcinoma cells and MEL-1 melanoma cells as controls, as described elsewhere (22, 23). Briefly, cells are harvested using EDTA/PBS and resuspended in RPMI 1640 medium with 10% FBS and 1% L-glutamine at $2\times10^7$ cells/ml. Cells are then aliquoted in duplicate for each antibody being tested at $6\times10^6$ cells/tube. Radiolabeled antibodies ($10^5$ cpm) are then added and incubated at 37° C. for 1 hr with shaking in a water bath. The cells are then washed with RPMI 1640 medium 3 times, and resuspended in 1 ml RPMI 1640 medium and counted in a well-type gamma counter. The % binding is then calculated. We will also determine the immunoreactivity of the radiolabeled MAbs using the procedure described by Lindmo et al. (24).

The in vitro chemical stabilities of radiolabeled conjugates can be evaluated by adding the solution of the radiolabeled antibody (50 μL–100 μL) to phosphate-buffered saline (pH 7.4, 500 μL), mixed and analyzed by SE-HPLC. A 20 μL aliquot is withdrawn at equal time intervals (1–24 h), over a 7 day period, and screened by SE-HPLC. A second sample is analyzed in the same way only at 37° C. All samples are screened by HPLC and the radioactivity content of the conjugates will be plotted against time, for each temperature.

To test the in vitro serum stability of the conjugates, the labeled conjugate solution (50 μL–100 μL) is added to 500 μL of human serum and the mixture is incubated at 37° C. At 1–24 h time intervals over a 7 day period, 20 μL aliquots are injected into the HPLC to follow the stability kinetics.

EXAMPLE VIII

IN VIVO BIODISTRIBUTION AND THERAPY STUDIES

1. Mouse model

Athymic nude female Balb/c mice, 5–8 weeks old, are kept under sterile conditions in a laminar flow room in cages with filter bonnets and are fed sterile mouse diet and sterilized tap water.

The mouse xenograft model, in which human colon cancer cell lines are transplanted to nude mice, is used to provide a situation similar to what will be encountered when radiolabeled antibodies are administered to humans. The tumor localization and tissue biodistribution of the radiolabeled antibodies are determined in nude mice bearing subcutaneous transplants of the LS174T human colon cancer cell line using tissue sampling and counting, or external scintigraphy. The use of a negative control human melanoma tumor (MEL-1) in nude mice will be used to control for in vivo specificity. The pharmacokinetics are determined in various tissues in mice and in rabbits. Therapeutic studies are conducted in nude mice with colon cancer xenografts and $^{131}$I, $^{67}$Cu, or $^{186}$Re beta-emitting radionuclides, conjugated to monoclonal antibodies, administered in an effort to determine the potential use of radiometal labeled antibodies for radioimmunotherapy.

Various groups of mice will be used. One group of athymic nude mice will receive a subcutaneous injection of $5 \times 10^6$ human colon cancer cells in a minimal volume of sterile culture media, generally 0.2 mL per mouse. Approximately 2–3 weeks later tumor growth will be seen of about 0.2–0.5 Cm$^2$. These animals will be injected by intraperitoneal or tail vein injection with radiolabeled antibody in sterile saline with 1% human serum albumin (sterile) and a total volume of 0.2 mL per mouse. These animals will be followed for 1–2 months and tumor growth and survival measured. In other groups of animals, biodistribution will be determined 1–5 days after injection. Mice will be euthanized by cervical dislocation. Just prior to euthanasia, the mouse will be anesthetized with ether and 0.5–1.0 mL of blood will be removed by cardiac puncture. All tail vein injections are performed on mice anesthetized with ether and after warming the tail to 37° C. with a heat lamp.

2. Biodistribution Studies

LS174T human colon tumor cells are harvested and suspended in serum-free growth medium. Cell viability is determined by trypan blue dye exclusion. Cells ($5 \times 10^6$ viable) is 0.2 mL medium are injected s.c. into the flank of nude mice. Growing tumors are measured with a vernier caliper at regular intervals. When the tumors are approximately 5–10 mm in diameter, the animals are given injections of radiolabeled antibodies and the biodistribution or tumor growth is determined. This model has been used effectively to demonstrate the relative efficiency of various radiolabeled monoclonal antibodies to retard tumor growth (19, 20). Ease of accessibility is a distinct benefit to using subcutaneously growing tumors for both biodistribution and radiotherapeutic studies. Subcutaneous tumors will be followed by direct measurements with vernier calipers. Width and length in millimeters will be determined and volumes calculated using the formula [(short dimension)$^2$×(long dimension)]/2. Growth of LS174T colorectal carcinoma xenografts is roughly logarithmic attaining 200–300 mm$^3$ in 8–12 days at which time the mice can be randomly assigned to groups of 6–10 animals for various therapeutic or biodistribution studies. Untreated xenografts will reach 1,000 mm$^3$ within another 8–9 days with a maximum size of 4,000 to 8,000 mm$^3$ by day 10–12 after randomization.

Quantification of the degree of localization of the various radiolabeled MAb CC49 preparations and determination of the level of their persistence within the tumor mass over time is determined using previously described procedures (22, 23, 25, 26). Nude mice bearing s.c. transplants of LS174T colon tumor are established as described above. Groups of 6 mice receive a single i.p. injection of 1 µCi of radiolabeled antibody. In selected experiments, dual radionuclide studies are performed in which the test antibody is labeled with one radionuclide and control antibody is labeled with another radionuclide, and they are injected simultaneously and the tissues counted at settings appropriate for the detection of the energies of the different radionuclides. Paired-label studies are essential to factor out differences in tumor size, antigen density and permeability as well as catabolic rate, that often exist among a group of experimental animals. At 1–5 days after injection, the mice are bled by cardiac puncture, dissected, and the tissues counted in a well-type gamma counter to determine the radioactivity in the tumors and normal tissues.

For each radiolabeled MAb, the following parameters are determined using previously published, standard methods: percent injected dose per organ (%ID/organ) and gram of tissue (%ID/g), tumor to normal tissue ratios and localization index. For scintigraphic imaging studies, mice with colon tumors are given i.p. injections of 100 µCi of $^{99m}$Tc, $^{186}$Re, or $^{67}$Cu-labeled antibody. Mice are anesthetized with sodium pentobarbital, and analog and digital images are acquired from the dorsal view with a Sopha DSX rectangular gamma camera equipped with a 4 mm pinhole collimator. Images are acquired for approximately 100,000 counts at day 1, after labeled antibody administration. The time required to reach this level is used at subsequent times. To permit visual assessment of relative tumor specificity, digital images are count normalized using a Sopha 32-bit microcomputer to produce visually identical levels of activity in a large region of interest covering the central torso. Mice are dissected following the images for distribution analysis.

3. Therapy studies

Therapy studies with radiolabeled antibodies are performed in nude mice bearing s.c. transplants of colon cancer cell lines. Animals are given one or more i.p. or i.v. injections of radiolabeled antibody when the tumors measure 0.25–0.99 cm$^2$ or 2 days following tumor cell injection. The animals are injected with a range of doses (0.1, 0.2, 0.3, 0.4 and 0.5 mCi) of radiolabeled MAb, to determine whether tumor growth is specifically inhibited or prevented. Fractionated RIT studies are also performed, by administering different quantities of radiolabeled antibody at varying time intervals.

An untreated control group and groups inoculated with unlabeled antibody or free radionuclide are included, but only using the most effective dose. Negative control tumors (MEL-1) are tested using the most effective dose of radiolabeled MAb. Animals with s.c. tumors are randomized into groups according to similar distributions of tumor sizes. A test group consists of 10 mice. Tumors are measured with calipers to determine surface area, approximated by multiplying length×width mm for 2–3 months to see if there is an inhibition of tumor growth, or regression, and cures. Tumor inhibition is assessed by evaluating changes in the mean increase of tumor size with time. Tumor regression is defined as 2 consecutive measurements of volume that are significantly less than the tumor volume on the day of treatment. Statistical significance of tumor regression is determined by the Fisher exact test.

Other groups of animals will be studied to see if there is an increase in the survival time of tumor-bearing animals inoculated with radiolabeled antibody, compared to control groups receiving unlabeled antibody, labeled control antibody, free radionuclide, or no treatment at all. Therapeutic efficacy is expressed as the percent change in mean survival time, or the mean of the log of survival time. Tumor size is modeled by regression as a function of days and groups are compared by the analysis of covariance. Survival is modeled by logistic regression as a function of days and the coefficients of the regression is compared across groups. Data from several experiments, each with the same treatment, is combined for purposes of numerical analysis. In addition, multiple comparisons among individual treatment groups are performed using the Bonferroni technique.

Tumor size: It is believed that tumor size is a function of treatment and time from treatment. If necessary, tumor size is log-transformed before analysis. The slope of tumor size as a linear function of time from treatment is compared across treatment groups. If there is no significant difference in slope between treatment groups, a test is made for difference in mean tumor size after adjusting for time as a covariate.

Survival Time: The median survival time is the primary measure of therapeutic efficacy. A long rank test is used to test differences in survival time between treatment groups; this nonparametric test does not assume any particular mathematical form of the survival function. Twenty animals per group is sufficient to test a 2.2-fold difference in survival times using a one-tailed test with 80% power and a significance level of 5%.

EXAMPLE IX

STABILITY AND PHARMOKINETICS STUDIES

Serum samples obtained from the ears of rabbits post-intravenous injection of radiolabeled antibodies are analyzed for radioactivity and mouse IgG to determine the stability and pharmacokinetics of the various radiometal chelated antibodies.

1. Mouse IgG in rabbit serum

The mouse IgG assay is a radiometric solid phase assay. Rabbit anti-mouse IgG coated polystyrene beads (2 µg/bead) are blocked by incubation with 1% each of normal goat and normal human serum for 1 hr. The beads are washed three times with a PBS containing 1% BSA and 0.005 M EDTA, pH 7.0 (PBE). The beads are stored at 4° C. until used. The standards are made from purified MAb diluted in PBE to a concentration ranging from 1–500 ng/mL. Standards, controls and rabbit serum (samples) either straight or at an appropriate dilution (100 µl) are incubated with a rabbit anti-mouse coated bead for 1 hr on a laboratory shaker. The beads are washed once with 5 ml of PBE and are then incubated with $^{125}$I-goat anti-mouse F(ab')$_2$ IgG (6 µCi/µg, 100,000 CPM). The incubation is continued for an additional hour on the shaker. The beads are washed again with 5 mL of PBE, and the bead associated radioactivity is determined in a Micromedic Automatic Gamma Counter interfaced with a SP/2 IBM Computer. A logit-log data reduction program is used to generate the standard plots and calculate the control and unknown values. All assays are performed in triplicate.

2. Pharmacokinetic analysis of rabbit serum

Pilot radiolabeling studies have been done with trisuccin conjugates. The in vivo stability of 186Re-FC49 was determined by injection of a 100 µCi aliquot i.v. into two NZW rabbits. The rabbits were bled from the other ear and radioactivity was determined in a 1 mL plasma sample FIG. 6. Below are the pharmacokinetic parameters determined in two rabbits using a two-compartment model.

| αT½ (hr) | βT½ (hr) | AUC (hr µg/ml) | MRT (hr) |
|---|---|---|---|
| 0.5 ± 0.009 | 19.7 ± 1.5 | .076 ± .00006 | 14.4 + 1.9 |

The data indicates that the $^{186}$Re-CC49 had an expected plasma clearance half-life in rabbits. Both $^{99m}$Tc-and $^{186}$Re-labeled CC49 conjugates were injected intraperitoneally into athymic nude mice implanted with LS174T human colon cancer xenografts. The animals were then subjected to imaging with a gamma camera. The $^{99m}$Tc-labeled CC49 had tumor localization at 15 h. The $^{186}$Re-CC49 had optimal imaging at the third and fourth day. Thus, the trisuccin agent can bind $^{99m}$Tc and $^{186}$Re to an intact monoclonal antibody with retention of immunoreactivity and ability to localize to colon cancer xenografts. Another potentially therapeutic radioactive metal that is included in the scope of this embodiment is $^{67}$Cu.

REFERENCES

The following references are hereby incorporated by reference herein to the extent that they teach, support or provide a basis for techniques relied upon in the foregoing disclosure.

(1) Waldmann, T. A. (1991) Monoclonal antibodies in diagnosis and therapy. *Science*, 252:1657.

(2) Schlom, J. (1986) Basic principles and applications of monoclonal antibodies in the management of carcinomas. *Cancer Res.* 46:3225.

(3) Cobb, L. M., and Humm, J. L. (1986) Radioimmunotherapy of malignancy using antibody targeted radionuclides. *Br. J. Cancer*, 54:863.

(4) Regoeczi, E. (1984) Methods of Protein Iodination. *Iodine Labeled Plasma Proteins*, pp 35–102, CRC Press, Inc., Boca-Raton, FL.

(5) Alauddin, M. M., Khawli, L. A., and Epstein, A. L. (1992) An improved method of direct labeling monoclonal antibodies with $^{99m}$Tc. *Nucl. Med. Biol.*, 19:445.

(6) Meares, C. F. (1986) Chelating agents for the binding of metal ions to antibodies. *Nucl. Med. Biol.*, 13:311.

(7) Engler, D., and Burger, A. G. (1984) The deiodination of the iodotyrosines and of their derivatives in man. *Endocr. Rev.*, 5:151.

(8) Sunberg, N. W., Meares, C. F., Goodwin, D. A., and Dismantic, C. I. (1974) Chelating agents for binding of metal ions to macromolecules. *Nature* (London), 250:587.

(9) Brechbiel, M. W., Gansow, O. A., Atcher, R. W., Schlom, J., Esteban, J., Simpson, D. E., and Colcher, D. (1986) Synthesis of 1-(p-isothiocyanatobenzyl) derivatives of DTPA and EDTA. Antibody labeling and tumor-imaging studies. *Inorg. Chem.*, 25:2772.

(10) Fritzberg, A. R., Abrams, P. G., Beaumier, P. L., Kasina, S., Morgan, A. C., Rao, T. N., Reno, J. M., Sanderson, J. A., Srinivasan, A., and Wilbur, D. S. (1988) Specific and stable labeling of antibodies with technetium-99m with a diamidedithiolate chelating agent. *Proc. Natl. Acad. Sci. USA*, 85:4025.

(11) Gagliardi, E., and Raber, H. (1962) Hydroxamsauren als analytische reagentien. *Monatsh. Chem.*, 93:360.

(12) Buckles, R. E., and Thelen, C. J. (1950) Qualitative determination of carboxylic esters. *Anal. Chem.*, 22:676.

(13) King, T. J., and Harrison, P. G. (1972) Crystal and molecular structure of triphenyltin N-benzoyl-N-phenylhydroxamate. *J. Chem. Soc. Chem. Comm.*, 815.

(14) Fournie-Zaluski, M.-C., Coulaud, A., Bouboutou, R., Chaillet, P., Devin, J., Waksman, G., Costentin, J., and Roques, P. (1985) New bidentates as full inhibitors of enkephalin-degrading enzymes: Synthesis and analgesic properties. *J. Med. Chem.*, 28:1158.

(15) Nakayama, M., Sawamura, H., Hasegawa, S., Harada, K., Sugii, A., Hara, M., Kinoshita, R., Ohyama, Y., Kojima, A., Tomiguchi, S., and Takahashi, M. (1992) Evaluation of Tc99m-hydroxamic acids as tumor imaging agents. *J. Nucl. Med.*, 33:988, Abstract.

(16) Arano, Y., Matsushima, H., Tagawa, M., Koizumi, M., Endo, R., Konishi, J. and Yokoyama, A. (1991), A novel bifunctional metagolizable linker for the conjugation of antibodies with radionuclides. *Bioconjugate Chem.*, 2:71–76.

(17) Newkome, G. R., Behera, R. K., Moorefield, C. N., and Baker, G. R. (1991) Cascade polymers: Syntheses and characterization of one-directional arborols based on adamantane. *J. Org. Chem.* 56, 7162.

(18) Sheehan, J. C., and Hess, G. P. (1955) A new method for forming peptide bonds. *J. Am. Chem. Soc.*, 77:1067.

(19) Konig, W., and Geiger, R. (1970) Racemisierung bei peptidsynthesen. *Chem. Ber.*, 103:2024.

(20) (Small grant): Neises, B. and Steglich, W. (1978), Simple method for the esterification of carboxylic acids. *Angew. Chem. Int. Ed. Engl.*, 17:522–523.

(21) Huet, F., Lechevallier, A., Pellet, M., Conia, J. M. (1978), Wet silica gel; a convenient reagent for deacetalization. *Synthesis*, 63.

(22) Buchsbaum, D. J., Lawrence, T. S., Roberson, P. L., Heidorn, D. B., Ten Haken R. K. and Steplewski, Z. (1993). Comparison of $^{131}$I- and $^{90}$Y-labeled monoclonal antibody 17-1A for treatment of human colon cancer xenografts. *Int. J. Radiat. Oncol. Biol. Phys.*, 25:629–638.

(23) Buchsbaum, D. J., Ten Haken RK, Heidorn, D. B., Lawrence T. S., et al. (1990). A Comparison of $^{131}$I-labeled monoclonal antibody 17-1A treatment to external beam irradiation on the growth of LS174T human colon carcinoma xenografts. *Int. J. Radiat. Oncol. Biol. Phys.*, 18:1033–1041.

(24) Lindmo, T., Boven, E., Cuttita, F., Fedorko, J., and Bunn, Jr. PA (1984). Determination of the immunoreactivity fraction of radiolabeled monoclonal antibodies by linear extrapolation to binding at infinite antigen excess. *J. Immunol. Meth.*, 72:77.

(25) Buchsbaum, D., Randall, B., Hanna, D., Chandler, R., Loken, M., Johnson, E. (1985). Comparison of the distribution and binding of monoclonal antibodies labeled with 131-iodine or 111-indium. *Eur. J. Nucl. Med.*, 10:398–402.

(26) Buchsbaum D. J., Hanna, D. E., Randall, B. C., Buchegger, F., Mach J-P (1985). Radiolabeleling of monoclonal antibody against carcinoembryonic antigen with 88Y and biodistribution studies. *Int. J. Nucl. Med. Biol.*, 12:79–82.

(27) Bodansky M., Riversible blocking of amino and carboxyl groups. Principles of *Peptide Synthesis*, pp. 59–107, Springer-Verlag, New York, 1984.

What is claimed is:

1. A bifunctional chelating compound comprising a protein conjugation function and a chelating function, the chelating compound further defined as 3-carboxypropyl N-[Tris[2-[[N-(benzyloxy)amino]carbonyl]ethyl]-methyl] succinamate.

2. A bifunctional chelating compound comprising a protein conjugation function and a chelating function, the chelating compound further defined as N,N-Bis[(N-hydroxylaminocarbonyl)methyl]-2-[2-(N-hydroxylaminocarbonyl)ethyl]glycine formylmethyl ester.

3. A bifunctional chelating compound comprising a protein conjugation function and a chelating function, the chelating compound further defined as N-[Tris[2-[(N-hydroxyamino)carbonyl]ethyl]-methyl]succinamic acid.

4. A bifunctional chelating compound comprising a protein conjugation function and a chelating function, the chelating compound further defined as N,N-bis (benzyloxyaminocarbonylmethyl)glycylglycine.

* * * * *

UNITED STATES PATENT AND TRADEMARK OFFICE
CERTIFICATE OF CORRECTION

PATENT NO. : 5,756,825
DATED : May 26, 1998
INVENTOR(S) : Ahmad Safavy, et al

It is certified that error appears in the above-indentified patent and that said Letters Patent is hereby corrected as shown below:

On the title page under item [75] Inventors, "Kazaeli" should read --Khazaeli--.

Signed and Sealed this

Twelfth Day of October, 1999

Q. TODD DICKINSON

*Attest:*

*Attesting Officer*  Acting Commissioner of Patents and Trademarks